(12) United States Patent
Liu (10) Patent No.: US 10,397,981 B2
(45) Date of Patent: Aug. 27, 2019

(54) ATOMIZING COMPONENT AND ELECTRONIC CIGARETTE

(71) Applicant: Shenzhen Kimsen Technology Co., Ltd, Shenzhen, Guangdong (CN)

(72) Inventor: Qiuming Liu, Guangdong (CN)

(73) Assignee: SHENZHEN KIMSEN TECHNOLOGY CO., LTD, Shenzhen (CN)

( * ) Notice: Subject to any disclaimer, the term of this patent is extended or adjusted under 35 U.S.C. 154(b) by 168 days.

(21) Appl. No.: 15/540,576

(22) PCT Filed: Dec. 29, 2014

(86) PCT No.: PCT/CN2014/095371
§ 371 (c)(1),
(2) Date: Jun. 29, 2017

(87) PCT Pub. No.: WO2016/106512
PCT Pub. Date: Jul. 7, 2016

(65) Prior Publication Data
US 2017/0359858 A1 Dec. 14, 2017

(51) Int. Cl.
*H05B 1/02* (2006.01)
*A24F 47/00* (2006.01)
*A61M 11/04* (2006.01)
*A61M 15/00* (2006.01)
*A61M 15/06* (2006.01)

(52) U.S. Cl.
CPC ......... *H05B 1/0291* (2013.01); *A24F 47/008* (2013.01); *A61M 15/0023* (2014.02); *A61M 15/06* (2013.01); *H05B 1/0277* (2013.01); *A61M 11/042* (2014.02); *A61M 2209/045* (2013.01); *H05B 1/0297* (2013.01)

(58) Field of Classification Search
None
See application file for complete search history.

*Primary Examiner* — Phu H Nguyen (57) ABSTRACT

The present application is disclosed an atomizing component and an electronic cigarette. The atomizing component comprises a light-permeable e-liquid storage sleeve. An atomizing core is detachably connected to an end of the e-liquid storage sleeve. A fastening element for restricting radial expansion of the e-liquid storage sleeve is sleeved at where the e-liquid storage sleeve is insertedly connected to the atomizing core. An end of a ventilation pipe opposite to the atomizing core is a smoke emitting outlet in communication with a suction nozzle. An e-liquid filler hole is extended from the end of the ventilation pipe provided with the smoke emitting outlet. The smoke emitting outlet and the e-liquid filler hole are located on planes of different heights; while e-liquid is being added, the outer circumferential wall of the ventilation pipe blocks the e-liquid splashed accidentally, thus preventing the e-liquid from being splashed into the ventilation pipe.

13 Claims, 6 Drawing Sheets

ATOMIZING COMPONENT AND ELECTRONIC CIGARETTE

FIELD OF THE INVENTION

The present application relates to a technical field of an electronic cigarette, and more particularly relates to an atomizing component and an electronic cigarette.

BACKGROUND OF THE INVENTION

At present, electronic cigarettes on the market comprises an electronic cigarette in which atomizing component is detachably connected to the battery assembly, or an electronic cigarette in which the battery assembly shares one outer casing with the atomizing component, and the atomizing component of the electronic cigarette comprises an atomizing core. When the electronic cigarette is working, the heat generating element in the atomizing core is heated to atomize e-liquid and smoke obtained by the atomization is discharged through an air passage to achieve effect of producing smoke.

The e-liquid required for the atomization of a refillable electronic cigarette is stored in the e-liquid storage chamber in the atomizing component. When the e-liquid in the e-liquid storage chamber is exhausted, new e-liquid can be refilled into the e-liquid storage chamber so that the electronic cigarette can continue to be used.

However, the smoke emitting outlet of the air passage of the atomizing component of an ordinary electronic cigarette is located in the e-liquid storage chamber and an e-liquid filling hole, and there is no isolation device to isolate the air passage from the e-liquid filling hole, then the operation of adding the e-liquid is extremely inconvenient. When the e-liquid is added to the e-liquid storage chamber of the atomizing component, the smoke can easily splash into the air passage or the e-liquid is easily to be mistakenly added to the air passage because the air passage is not sealed or the air passage is not isolated from the e-liquid filling hole, then it affects an atomizing effect of a heating wire assembly within the atomizing component and even makes the whole electronic cigarette scrapped.

SUMMARY OF THE INVENTION

The technical problem to be solved by the present invention is to provide an atomizing component and an electronic cigarette aiming at the above-mentioned drawbacks of the prior art.

TECHNICAL SOLUTION OF TECHNICAL PROBLEMS

Technical Solution

The technical scheme for solving the technical problem of the invention is shown as following:

Provide an atomizing component configured to form an electronic cigarette with a battery assembly, comprising a light-permeable e-liquid storage sleeve, an atomizing core is detachably connected to an end of the e-liquid storage sleeve, a fastening element configured for restricting radial expansion of the e-liquid storage sleeve is sleeved at a position of the e-liquid storage sleeve, the position of the e-liquid storage sleeve is configured to be insertedly connected to the atomizing core;

An e-liquid filling hole is defined on one end surface of the other end of the e-liquid storage sleeve, a connecting mechanism is defined at the e-liquid filling hole, one end of the connecting mechanism is detachably connected to the e-liquid storage sleeve, the other end of the connecting mechanism is connected to a suction nozzle; a ventilation tube is sleeved in the e-liquid storage sleeve, two ends of the ventilation tube are elastically and hermetically connected to the atomizing core and the connecting mechanism, respectively, an e-liquid storage chamber for storing e-liquid is formed between the ventilation tube and the e-liquid storage sleeve;

An end of the ventilation tube opposite to the atomizing core is provided with a smoke emitting outlet in communication with the suction nozzle, the end of the ventilation tube provided with the smoke emitting outlet extends from the e-liquid filling hole so that the smoke emitting outlet of the ventilation tube is higher than the e-liquid filling hole when the atomizing component is placed vertically to add e-liquid;

The atomizing core comprises an atomizing sleeve, an end of the atomizing sleeve extends outside the e-liquid storage sleeve to detachably connect to the battery assembly, the end of the atomizing sleeve is provided with an atomizing electrode assembly electrically connected to the battery assembly, an atomizing chamber is formed in the atomizing sleeve, and a heating wire assembly electrically connected to the atomizing electrode assembly is received in the atomizing chamber.

In the atomizing component of the present invention, the smoke emitting outlet of the ventilation tube is at least 1.5 mm higher than the e-liquid filling hole when the atomizing component is placed vertically to add the e-liquid.

In the atomizing component of the present invention, the suction nozzle is provided with a condensation chamber communicating with the ventilation tube, a chamber wall of the condensation chamber is provided with an air outlet for discharging smoke, so that condensed e-liquid can be stored in the condensation chamber when the smoke atomized by the heating wire assembly flows to the air outlet through the ventilation tube.

In the atomizing component of the present invention, wherein the connecting mechanism comprises a first connecting tube, the ventilation tube extends into the first connecting tube and is detachably connected to an inner side wall of the first connecting tube, and an outer side wall of an end of the first connecting tube is detachably connected to the suction nozzle, the end of the first connecting tube is close to the suction nozzle.

In the atomizing component of the present invention, the connecting mechanism further comprises a sealing circle piece and a pressing piece which are respectively fixed to an inner side wall of the first connecting tube, the sealing circle piece is elastically abutted against at an end of the ventilation tube, the pressing piece is defined at a side of the sealing circle piece facing toward the suction nozzle and is abutted against the sealing circle piece.

In the atomizing component of the present invention, the connecting mechanism comprises a second connecting tube arranged outside the e-liquid storage sleeve, an end of the second connecting tube extending outside the e-liquid storage sleeve is detachably connected to the suction nozzle, the second connecting tube is provided with a clamping member for fixing the ventilation tube; the clamping member is provided with a perforation for the ventilation tube to pass through, and a plurality of e-liquid inlet holes for adding the e-liquid, the plurality of the e-liquid inlet holes are distributed around the perforation.

In the atomizing component of the present invention, the clamping member comprises a main body and a connecting ring, an end of the connecting ring is fixed on a periphery of the main body, an outer side wall of the connecting ring is abutted against an inner side wall of the second connecting tube, the perforation and the e-liquid inlet holes are both defined on the main body, a limit projection is convexly defined on an outer side wall of the ventilation tube, the limit projection is configured for limiting the ventilation tube to moving toward a side close to the suction nozzle, the limit projection is abutted against a side edge of an end of the perforation, the end of the perforation is opposite to the suction nozzle.

In the atomizing component of the present invention, the atomizing core further comprises an atomizing cover arranged on the atomizing sleeve and the ventilation tube and abutted against the heating wire assembly, one end of the ventilation tube passes through the atomizing cover and extends into the atomizing chamber.

In the atomizing component of the present invention, one end of the ventilation tube is detachably connected to the atomizing cover, the end of the ventilation tube is opposite to the suction nozzle, a stopper flange is convexly defined on an outer side wall of the ventilation tube, the stopper flange is configured for limiting the ventilation tube to moving toward a side opposite to the suction nozzle, the stopper flange is abutted against an end of the atomizing cover.

In the atomizing component of the present invention, the atomizing sleeve comprises a first case and a second case which are detachably connected to each other, the first case is defined within the e-liquid storage chamber, the heating wire assembly is mounted on the first case, one end of the second case extending outside the e-liquid storage chamber is detachably connected to the battery assembly; and the atomizing core further comprises a pressing member abutted against the heating wire assembly, and a sealing ring sleeved on a joint between the pressing member and the first case, the ventilation tube is sleeved outside the pressing piece and elastically abutted against the sealing ring, the pressing member is a hollow structure and is communicated with the ventilation tube.

In the atomizing component of the present invention, an air inlet hole (313) is defined on a peripheral wall of an end of the atomizing sleeve extending outside the e-liquid storage sleeve, the air inlet hole communicated with the atomizing chamber is configured for inletting air and discharging e-liquid in the atomizing chamber.

In the atomizing component of the present invention, an end of a side wall of the atomizing sleeve close to the suction nozzle is axially provided with two mounting grooves, the two mounting grooves are spaced from each other, arranged opposite to each other and communicated with the e-liquid storage chamber, the heating wire assembly is arranged in the two mounting grooves.

The present invention further provides an electronic cigarette comprising a battery assembly and an atomizing component which are connected to each other, the atomizing component comprises a light-permeable e-liquid storage sleeve, an atomizing core is detachably connected to an end of the e-liquid storage sleeve, a fastening element configured for restricting radial expansion of the e-liquid storage sleeve is sleeved at where the e-liquid storage sleeve is insertedly connected to the atomizing core;

an e-liquid filling hole is defined on one end surface of the other end of the e-liquid storage sleeve, a connecting mechanism is defined at e-liquid filling hole, one end of the connecting mechanism is connected to the e-liquid storage sleeve, the other end of the connecting mechanism is detachably connected to a suction nozzle; a ventilation tube is sleeved in the e-liquid storage sleeve, two ends of the ventilation tube are elastically and hermetically connected to the atomizing core and the connecting mechanism, respectively, an e-liquid storage chamber for storing the e-liquid is formed between the ventilation tube and the e-liquid storage sleeve;

an end of the ventilation tube opposite to the atomizing core is a smoke emitting outlet in communication with the suction nozzle, the end of the ventilation tube which is provided with the smoke emitting outlet extends from the e-liquid filling hole so that the smoke emitting outlet of the ventilation tube is higher than the e-liquid filling hole when the atomizing component is placed vertically to add e-liquid; and the atomizing core comprises an atomizing sleeve, an end of the atomizing sleeve extends outside the e-liquid storage sleeve to detachably connected to the battery assembly, an end of the atomizing sleeve is provided with an atomizing electrode assembly electrically connected to the battery assembly, an atomizing chamber is formed in the atomizing sleeve, and a heating wire assembly electrically connected to the atomizing electrode assembly is received in the atomizing chamber.

ADVANTAGES OF THE PRESENT INVENTION

Advantages

In conclusion, the atomizing component and the electronic cigarette according to the present invention have the following advantageous effects: First, one end of the ventilation tube near the suction nozzle extends outside the e-liquid filling hole, namely, the smoke emitting outlet of the ventilation tube and the e-liquid filling hole of the e-liquid storage sleeve are positioned on planes with different heights, so that the smoke emitting outlet of the ventilation tube is higher than the e-liquid filling hole of the e-liquid storage sleeve, when the atomizing component is placed vertically to add smoke from the e-liquid filling hole. An outer side wall of the ventilation tube blocks the e-liquid so that the e-liquid can be prevented from splashing into the ventilation tube even if the e-liquid splash occurs accidently during the addition of the e-liquid; and one end of the e-liquid storage sleeve is detachable connected to the atomizing core so that it can be easily replaced when the atomizing core is damaged, and it also avoids problems, such as, a battery damage, a short circuit and other issues, which are caused by that the e-liquid easily leaks from the atomizing core into the battery assembly due to frequent removals of the atomizing core, when the e-liquid filling hole is provided at an insertion opening of the e-liquid storage sleeve at the atomizing core. Meanwhile, the means of adding e-liquid at the suction nozzle allows the atomizing assembly to be placed directly on a support subject to add the e-liquid when the e-liquid is added, thereby facilitating the use and more in accordance with a user's habit. Next, since the height difference between the smoke emitting outlet of the ventilation tube and the e-liquid filling hole of the e-liquid storage sleeve is 1.5 mm, the smoke emitting outlet of the ventilation tube is physically separated from the e-liquid filling hole of the e-liquid storage sleeve and has a distinct position, it can be convenient for the user to add e-liquid. Finally, the e-liquid storage sleeve is provided with a fastening element at a position insertedly connected to the atomizing core, the fastening element is arranged outside the e-liquid storage sleeve, and the fastening element can not only prevent an expansion of the e-liquid storage sleeve, but also can enhance connection strength between the e-liquid storage sleeve and the atomizing core, so as to prevent the atomizing core from dropping from the e-liquid storage sleeve.

BRIEF DESCRIPTION OF THE DRAWINGS

Description of the Drawings

The present invention will now be described in further detail with reference to the accompanying drawings and embodiments, the accompanying drawings as shown as following.

DETAILED DESCRIPTION OF THE PREFERRED EMBODIMENT

The Preferred Embodiment of the Present Invention

The present invention will be described in further detail with reference to the accompanying drawings and the embodiments in order to make the objectives, technical solutions and advantages of the present invention more clearly understood. It is to be understood that the specific embodiments described herein are merely illustrative of the present invention and are not intended to limit the present invention.

Figure 1:
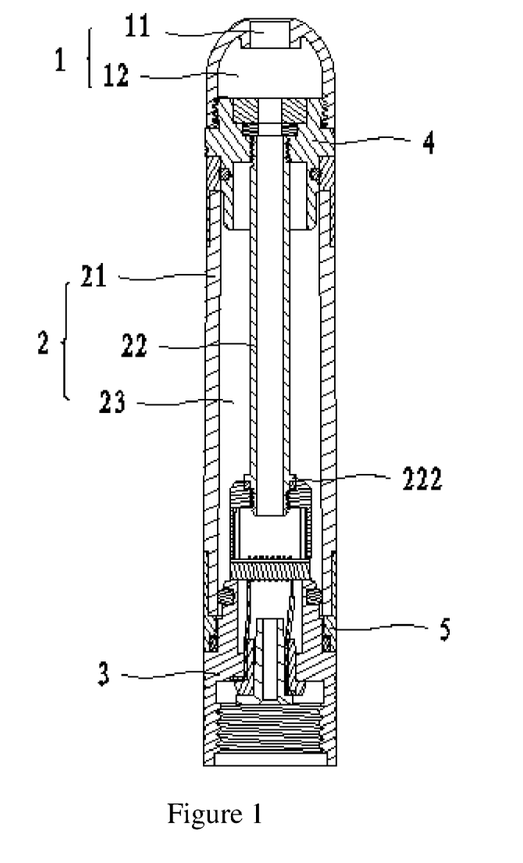
FIG. 1 is a schematic structural view of an atomizing component provided in one of the preferred embodiments of the present invention.

FIGS. 1, 2, 3 and 4 show an atomizing component provided by one of preferred embodiments of the present invention, the atomizing component is configured for forming an electronic cigarette with a battery assembly (not shown in the drawings), as shown in FIG. 1, the atomizing component comprises a light-permeable e-liquid storage sleeve 21, an atomizing core 3 is detachably connected to an end of the e-liquid storage sleeve 21, a fastening element 5 configured for restricting radial expansion of the e-liquid storage sleeve 21 is sleeved at a position of the e-liquid storage sleeve 21, the position of the e-liquid storage sleeve 21 is configured to be insertedly connected to the atomizing core 3.

Figure 2:
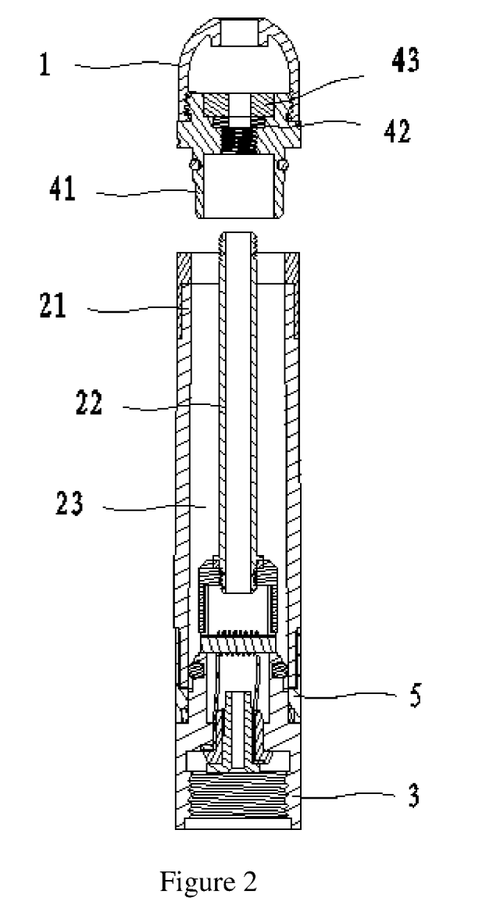
FIG. 2 is an exploded view of an atomizing component provided in one of the preferred embodiments of the present invention.

As shown in FIG. 2, an e-liquid filling hole is defined on one end surface of the e-liquid storage sleeve 21, a connecting mechanism 4 is defined at the e-liquid filling hole, one end of the connecting mechanism 4 is detachably connected to the e-liquid storage sleeve 21, the other end of the connecting mechanism 4 is detachably connected to a suction nozzle 1; a ventilation tube 22 is sleeved in the e-liquid storage sleeve 21, two ends of the ventilation tube 22 are elastically and hermetically connected to the atomizing core 3 and the connecting mechanism 4, respectively, an e-liquid storage chamber 23 for storing e-liquid is formed between the ventilation tube 22 and the e-liquid storage sleeve 21.

Figure 3:
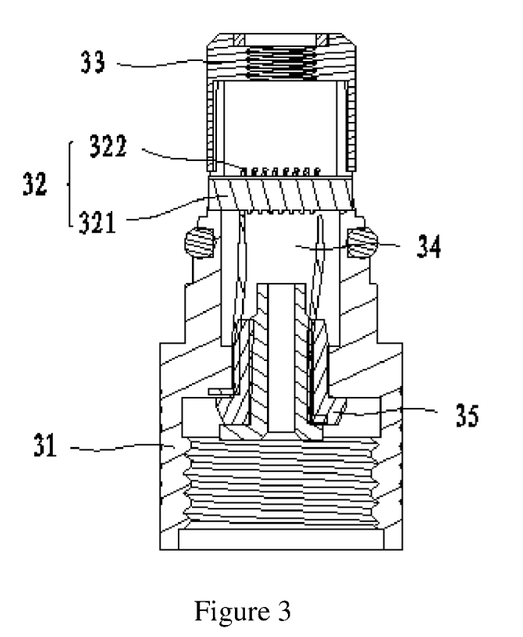
FIG. 3 is a schematic structural view of an atomizing core of the atomizing component of FIG. 1.

The end of the ventilation tube 22 opposite to the atomizing core 3 is provided with a smoke emitting outlet in communication with the suction nozzle 1, the end of the ventilation tube 22 provided with the smoke emitting outlet extends from the e-liquid filling hole so that the smoke emitting outlet of the ventilation tube 22 is higher than the e-liquid filling hole when the atomizing component is placed vertically to add e-liquid As shown in FIG. 3, the atomizing core 3 comprises an atomizing sleeve 31, an end of the atomizing sleeve 31 extends outside the e-liquid storage sleeve 21 to detachably connect to the battery assembly, an end of the atomizing sleeve 31 is provided with an atomizing electrode assembly 35 electrically connected to the battery assembly, an atomizing chamber 34 is formed in the atomizing sleeve 31, and a heating wire assembly 32 electrically connected to the atomizing electrode assembly 35 is received in the atomizing chamber 34. The fastening element 5 may be provided to be integrally formed with the atomizing sleeve 31, and the structure thereof is not particularly limited thereto.

In order to avoid that the e-liquid is dropped into the ventilation tube 22 to affect user's experience when e-liquid is added from the e-liquid filling hole, in the present embodiment, one end of the ventilation tube 22 near the suction nozzle 1 extends outside the e-liquid filling hole, namely, the smoke emitting outlet of the ventilation tube 22 and the e-liquid filling hole of the e-liquid storage sleeve 21 are positioned on planes with different heights, so that the smoke emitting outlet of the ventilation tube 22 is higher than the e-liquid filling hole of the e-liquid storage sleeve 21, when the atomizing component is placed vertically to add smoke from the e-liquid filling hole. An outer side wall of the ventilation tube blocks the e-liquid so that the e-liquid can be prevented from splashing into the ventilation tube 22 even if the e-liquid splash occurs accidently during the addition of the e-liquid. Since the height difference between the smoke emitting outlet of the ventilation tube 2 and the e-liquid filling hole of the e-liquid storage sleeve 21 is 1.5 mm, the smoke emitting outlet of the ventilation tube 22 is physically separated from the e-liquid filling hole of the e-liquid storage sleeve 21 and has a distinct position, it can be convenient for the user to add e-liquid.

Preferably, the smoke emitting outlet of the ventilation tube 22 is at least 1.5 mm higher than the e-liquid filling hole when the atomizing component is placed vertically and the e-liquid is added from the e-liquid filling hole of the e-liquid storage sleeve 21. In this embodiment, the smoke emitting outlet of the ventilation tube 22 is 2 mm higher than the e-liquid filling hole.

Further, since the atomizing core 3 is inserted into the e-liquid storage sleeve 21 and is interference fitted with the e-liquid storage sleeve 21, the e-liquid storage sleeve 21 is liable to radially expand to be broken at a position to which the atomizing core 3 is insertedly connected, thereby affecting the fastening fit between the atomizing core 3 and the e-liquid storage sleeve 21. In addition, the heat released by the atomization of the heating wire assembly 32 tends to cause the atomizing sleeve 1 to be thermally expanded and contracted to cause deformation, thereby affecting the fastening fit between the atomizing core 3 and the e-liquid storage sleeve 21.

In the present invention, the fastening element 5 is sleeved at a position of the e-liquid storage sleeve 21, the position of the e-liquid storage sleeve 21 is configured to be insertedly connected to the atomizing core 3, the fastening element 5 is provided outside the e-liquid storage sleeve 21, and the fastening member 5 not only can prevent the radial expansion of the e-liquid storage sleeve 21, but also can enhance connection strength between the e-liquid storage sleeve 21 and the atomizing core 3, so that the atomizing core 3 is prevented from dropping from the e-liquid storage sleeve 21. Preferably, the fastening member 5 is a metal ring.

A specific structure of the connecting mechanism 4 will be described in detail with reference to the embodiment shown in FIGS. 1 and 2.

As shown in FIG. 2, the connecting mechanism 4 comprises a first connecting tube 41, a sealing circle piece 42 and a pressing piece 43, both of the sealing circle piece 42 and the pressing piece 43 are fixed to an inner side wall of the first connecting tube 43.

One end of the first connecting tube 41 is detachably connected to the suction nozzle 1, and the other end of the first connecting tube 41 is inserted into the e-liquid storage sleeve 21, the ventilation tube 41 extends into the first connecting tube 41 and is detachably connected to an inner side wall of the first connecting tube 41.

In the present embodiment, the suction nozzle 1 is detachably connected to the first connecting tube 41 by a screw structure. Specifically, an outer side wall of an end of the first connecting tube 41 is provided with an external thread, the outer side wall of the end faces toward the suction nozzle 1, an internal thread fitting to the external thread is defined on the suction nozzle 1.

Further, the first connecting tube 41 is rotationally inserted in the e-liquid storage sleeve 21, and the first connecting tube 41 and the ventilation tube 22 are also detachably connected by a screw structure. Specifically, an inner wall of the first connecting tube 41 is provided with an internal thread, and the end of the ventilation tube 22 is provided with an external thread fitting with the internal thread, the end faces toward the suction nozzle 1.

Preferably, a sealing member (not labeled in figures) for sealing the e-liquid is defined at an outer side wall of the first connecting tube 41 configured to be insertedly connected to the e-liquid storage sleeve 21, so as to prevent the e-liquid from leaking from a gap between the first connecting tube 41 and the e-liquid storage sleeve 21.

It is preferable that a knurling structure for non-slip may be provided on an outer side wall of the first connecting tube 41 in order to facilitate a user's detachment of the first connecting tube 41.

The sealing circle piece 42 is fixed to an inner side wall of the first connecting tube 41 and elastically abutted against an end of the ventilation tube 22 so as to prevent the e-liquid in the e-liquid storage chamber 23 from leaking from a gap between the ventilation tube 22 and the first connecting tube 41 and then being inhaled by the user to affect the user experience.

The pressing piece 43 is fixed to the inner side wall of the first connecting tube 41, and the pressing piece 43 is defined on a side of the sealing circle piece 42 facing toward the suction nozzle 1 and abutted against the sealing circle piece 42. In the present embodiment, the pressing piece 43 is mainly used for fixing the sealing circle piece 42, so as to prevent the sealing circle piece 42 from being pushed out by the ventilation tube 22. When the atomizing core 3 is replaced, the ventilation tube 22 is forced to move to the side of the suction nozzle 1 along the axial direction of the e-liquid storage sleeve 21, then the seal ring 42 is upwardly pushed, resulting in that the seal ring 42 is easily pushed out by the ventilation tube 22, thereby affecting a sealing effect of the seal ring 42.

The specific structure of the suction nozzle 1 and an e-liquid cup assembly 2 will be described in detail with reference to the embodiments shown in FIGS. 1 and 2.

As shown in FIG. 1, the suction nozzle 1 is detachably connected to an end of the first connecting tube 41 so that the user is convenient to clean the suction nozzle 1. The suction nozzle 1 is provided with an air outlet 11 and a condensation chamber 12, the air outlet 11 is defined at the bottom wall of the condensation chamber 12 and is configured for discharging smoke.

Preferably, the condensation chamber 12 is defined in the suction nozzle 1, so that condensed e-liquid can be stored in the condensation chamber 12 when the smoke atomized by the heating wire assembly 32 flows to the air outlet 11 through the ventilation tube 22, then the e-liquid can be prevent from being inhaled by the user. Since the suction nozzle 1 is detachably connected to the first connecting tube 41, the suction nozzle 1 can be removed at regular time to clean the e-liquid remaining in the condensation chamber 12, so as to prevent the user from inhaling the e-liquid.

Preferably, an outer end surface of the suction nozzle 1 is spherical so that the suction nozzle 1 is more beautiful, and the suction nozzle 1 with the outer end surface is more convenient to be cleaned. In addition, since the suction nozzle 1 having a spherical end surface is structurally stable, it is possible to prevent the suction nozzle 1 from being easily deformed to drop off when hard objects such as teeth in an oral cavity clamp on the suction nozzle 1.

It is preferable that the suction nozzle 1 and the first connecting tube 41 are metallic material products in this embodiment, and it is possible to prevent the suction nozzle 1 from being easily dropped off when the hard objects such as the teeth of the oral cavity clamp on the first connecting tube 41, therein the metal may be copper, iron or steel, and is not particularly limited thereto.

As shown in FIG. 2, the e-liquid cup assembly 2 mainly comprises an e-liquid storage sleeve 21, a ventilation tube 22, and an e-liquid storage chamber 23. The e-liquid storage sleeve 21 has a substantially cylindrical structure, and the connecting mechanism 4 and the atomizing core 3 are connected to two ends of the e-liquid storage sleeve 21, respectively. In order to facilitate the user to view the amount of remaining e-liquid in the e-liquid storage chamber 23, in the present embodiment, the e-liquid storage sleeve 21 is made of a light-permeable material.

The ventilation tube 22 is provided in the e-liquid storage sleeve 21 in the axial direction of the e-liquid reserving case 21, and an airflow passage for airflow to flow to the suction nozzle 1 is enclosed in the ventilation tube 22, and two ends of the ventilation tube 22 are respectively inserted in the connecting mechanism 4 and the atomizing core 3. Further, the e-liquid storage chamber 23 is formed between the e-liquid storage sleeve 21 and the ventilation tube 22, and the e-liquid atomized by the atomizing core 3 is stored in the atomizing chamber 23.

A specific structure of the atomizing core 3 will be described in detail with reference to the embodiments shown in FIGS. 3 and 4.

As shown in FIG. 3, the atomizing core 3 mainly comprises an atomizing sleeve 31, the heating wire assembly 32, an atomizing cover 33, an atomizing chamber 34, and an atomizing electrode assembly 35.

The atomizing chamber 34 is provided inside the atomizing sleeve 31 and communicates with the ventilation tube 22, and the heating wire assembly 32 is accommodated in the atomizing chamber 34; the atomizing cover 33 is sleeved on the atomizing sleeve 31 and the ventilation tube 22, and is abutted against the heating wire assembly 32, one end of the ventilation tube 22 passes through the atomizing cover 33 and extends into the atomizing chamber 34.

Figure 4:
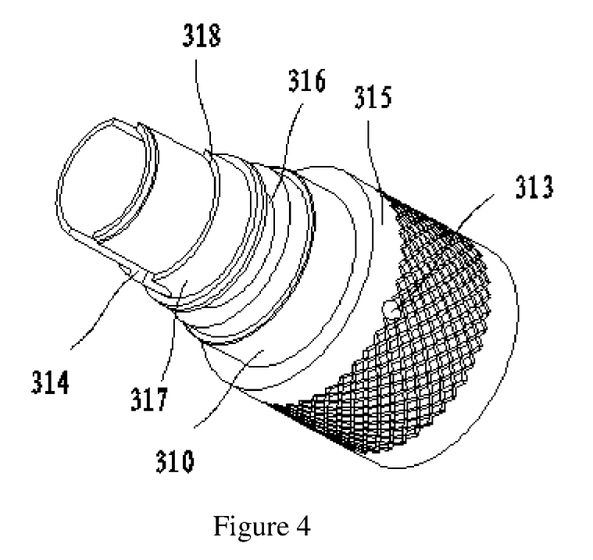
FIG. 4 is a schematic structural view of an atomizing sleeve of the atomizing core shown in FIG. 3.

As shown in FIG. 4, one end of the atomizing sleeve 31 is detachably connected to the e-liquid storage sleeve 21, and the other end is detachably connected to the battery assembly. Specifically, the atomizing sleeve 31 has an atomizing sleeve main body 310 which is generally a hollow staircase-like structure. The atomizing sleeve main body 310 is provided with an air inlet hole 313, mounting grooves 314, a stopper table 315, an annular groove 316, a projection 317 and a stopper projection 318.

The air inlet hole 313 is provided at one end of the atomizing sleeve main body 310 which extends outside the e-liquid storage sleeve 21, and the air inlet hole 313 communicates with the atomizing chamber 34. The air inlet 313 is mainly used for inletting air and discharging e-liquid in the atomizing chamber 34. Since the air inlet hole 313 is located outside the e-liquid storage sleeve 21, the airflow directly passes through the air inlet hole 313 to enter the atomizing chamber 34 without causing noise.

An end of the atomizing sleeve main body 310 close to the suction nozzle 1 is provided with the mounting grooves 314. In the present embodiment, the mounting grooves 314 comprises two mounting grooves 314, the two mounting grooves 314 are spaced from each other, arranged opposite to each other and communicated with the e-liquid storage chamber 23, an e-liquid guider 321 of the heating wire assembly 32 is arranged in the two mounting grooves 314 and fixed to the bottom of the two mounting grooves 314.

The stopper table 315 is convexly defined on an outer wall of the atomizing sleeve main body 310 so as to prevent the atomizing core 3 from blocking the air inlet hole 313 during an assembling process. Specifically, the stopper table 315 is abutted against a side edge of an end of the e-liquid storage sleeve 21 during the assembly process of the atomizing core 3, since the air inlet hole 313 is located on a side of the stopper table 315 opposite to the suction nozzle 1, it is possible to prevent the air inlet hole 313 from being blocked during the assembling process.

It is preferable that a non-slip knurling structures may be provided on an outer circumference of the stopper table 315 in order to facilitate the user to disassemble and assemble the atomizing core 3.

Preferably, a sealing piece (not labeled in figures) may be provided on the atomizing sleeve main body 310 in order to prevent the e-liquid from leaking from a connection point between the atomizer body 310 and the e-liquid storage sleeve 21. Specifically, in the present embodiment, the atomization sleeve main body 310 is provided with an annular groove 316 in an outer peripheral wall of the e-liquid storage sleeve 21, and the sealing piece is fixed in the annular groove 316 and is elastically abutted against an inner wall of the e-liquid storage sleeve 21, in order to achieve sealing effect.

Preferably, in order to well support the heating wire assembly 32, the atomizing sleeve main body 310 is provided with the projection 317 for supporting the heating wire assembly 32, one end of the projection 317 is fixed to the bottom of the mounting groove 314 while the other end of the projection 317 extends opposite to the axial direction of the atomizing sleeve main body 310. By providing the projection 317, it is possible to prevent a side wall for supporting the heating wire assembly 32 from being too thin and the heating wire assembly 32 sliding into the atomizing chamber 34.

Preferably, combined with FIG. 3, since the atomizing cover 33 is provided on the atomizing sleeve 31 and is abutted against the heating wire assembly 32, in order to prevent the atomizing cover 33 from over-pressing the heating wire assembly 32, the sleeve body 310 is provided with the stopper projection 318 which is convexly defined on the atomizing sleeve main body 310 and abutted against an end surface of the atomizing cover 33.

As shown in FIG. 3, the heating wire assembly 32 comprises the e-liquid guider 321 and a heating wire 322, the e-liquid guider 321 is made of e-liquid absorbing materials and is fixed to the bottom of the mounting grooves 314, two ends of the e-liquid guider 321 extend into the e-liquid storage chamber 23, the heating wire 322 is wound around the e-liquid guider 321 and electrically connected to the battery assembly. Since the heating wire assembly 32 is a conventional means of the prior art, the specific structure thereof will not be described here.

As shown in FIG. 3, the atomizing cover 33 is provided with an accommodating cavity (not labeled) penetrating the atomizing cover 33 along the axial direction, one end of the atomizing cover 33 opposite to the suction nozzle 1 is sleeved on the atomizing sleeve main body 310 and is abutted against the stopper projection 318, the ventilation tube 22 (shown in FIG. 2) is inserted from one end of the atomizing cover 33 near the suction nozzle 1 and is detachably connected to the accommodating cavity by a threaded structure.

Preferably, as shown in FIG. 1, a stopper flange 222 is convexly defined on an outer side wall of the ventilation tube 22, the stopper flange 222 is configured for limiting the ventilation tube 22 to moving toward a side opposite to the suction nozzle 1. When the user connects the connecting mechanism 4 to the ventilation tube 22, the ventilation tube 22 is forced to move the side opposite to the suction nozzle 1, then the stopper flange 222 prevents the ventilation tube 22 from moving toward the side opposite to the suction nozzle 1, thereby the stability of the connection between the ventilation tube 22 and the connecting mechanism 4 can be ensured.

It is preferable that a sealing piece (not labeled in figures) may be provided at the end where the atomizing cover 33 is connected to the ventilation tube 22 in order to prevent leakage of the e-liquid from the connection between the ventilation tube 22 and the atomizing cover 33. In this embodiment, the sealing piece is fixed to a surface of an end surface of the atomizing cover 33 facing toward the suction nozzle 1 and is elastically abutted against an outer peripheral wall of the ventilation tube 22 to function as a seal.

As shown in FIG. 3, the atomizing electrode assembly 35 is located at an end of the atomizing sleeve 31 opposite to the suction nozzle 1 and is electrically connected to the battery assembly and the heating wire assembly 32. In the present embodiment, the atomizing sleeve 31 is an external electrode electrically connected to the battery assembly, and the atomizing electrode assembly 35 comprises an insulating member (not labeled) and an inner electrode (not labeled) which are successively embedded in the atomizing sleeve 31 from outside to inside, the inner electrode is electrically connected to the battery assembly.

It is to be understood that, in other embodiments, the atomizing electrode assembly 35 may also be made of other conductive structures, such as the atomizing sleeve 31, which is a non-conductive material, and the atomizing electrode assembly 35 comprises, an outer electrode which is electrically connected to the battery assembly, an insulating member, and an internal electrode which is electrically connected to the battery assembly, the outer electrode, the insulating member and the internal electrode are embedded in the atomizing sleeve 31 from outside to inside.

In the present embodiment, the atomizing core 3 mainly comprises the atomizing sleeve 31, the atomizing chamber 34 is defined inside the atomizing sleeve 31 and communicates with the ventilation tube 22, and the heating wire assembly 32 is accommodated in the atomizing chamber 34; the atomizing cover 33 covers on the atomizing sleeve 31 and the ventilation tube 22 and is abutted against the heating wire assembly 32, and one end of the ventilation tube 22 passes through the atomizing cover 33 and extends into the atomizing chamber 34. It is to be understood that the atomizing core 3 of the present application is not limited to the above-described structure, and may be other structures as long as it can atomize the e-liquid.

The present invention also provides an electronic cigarette comprising an atomizing component and a battery assembly, wherein the atomizing component is the atomizing component described above, and the battery assembly is a conventional battery assembly in the prior art, and the specific structure and function of the battery assembly are not repeated here.

FIGS. 5, 6, 7, 8 and 9 show an atomizing component of a second preferred embodiment of the present invention, which differs from the first embodiment in structures of the connecting mechanism 4 and the atomizing core 3.

Figure 5:
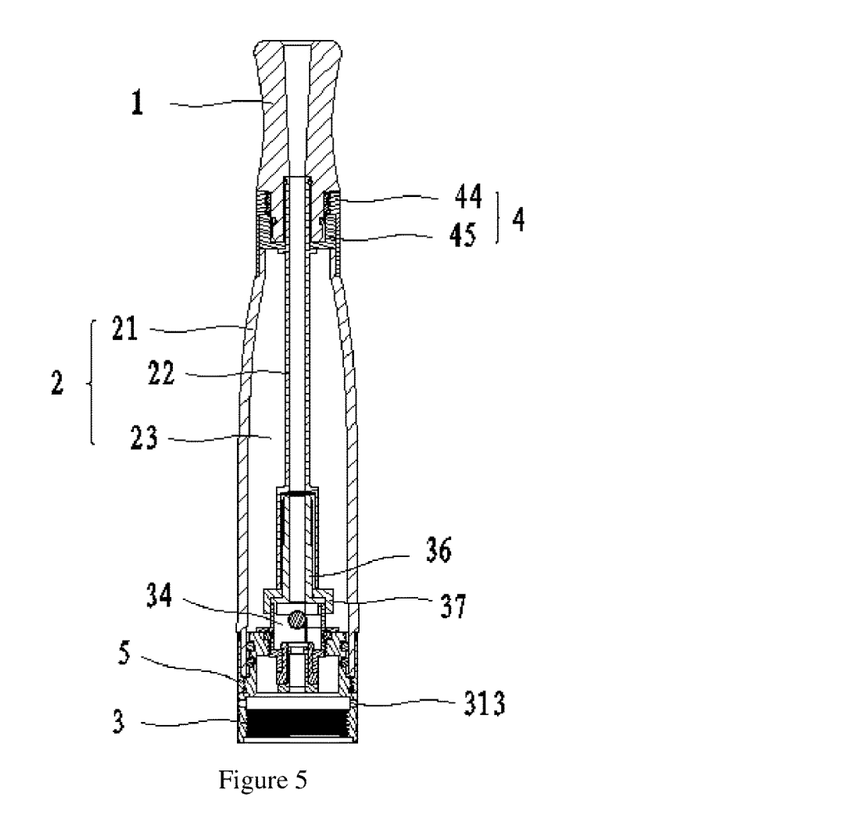
FIG. 5 is a schematic structural view of an atomizing component provided in the second embodiment of the present invention.

As shown in FIG. 5, the connecting mechanism 4 comprises a second connecting tube 44 and a clamping member 45 which is embedded in the second connecting tube 44.

One end of the second connecting tube 44 is fixed out the e-liquid storage sleeve 21, and the other end of the second connecting tube 44 is detachably connected to a suction nozzle 1, the ventilation tube 22 passes through the clamping member 45 and extends out of an e-liquid filling hole of the e-liquid storage sleeve 21.

In the present embodiment, the suction nozzle 1 is detachably connected to the second connecting tube 44 by a screw structure. Specifically, an inner side wall of one end of the second connecting tube 44 is provided with an internal thread, the end of the second connecting tube 44 faces toward the suction nozzle 1, an outer side wall of the suction nozzle 1 is convexly provided with an external thread which is adapted to the internal thread.

Figure 6:
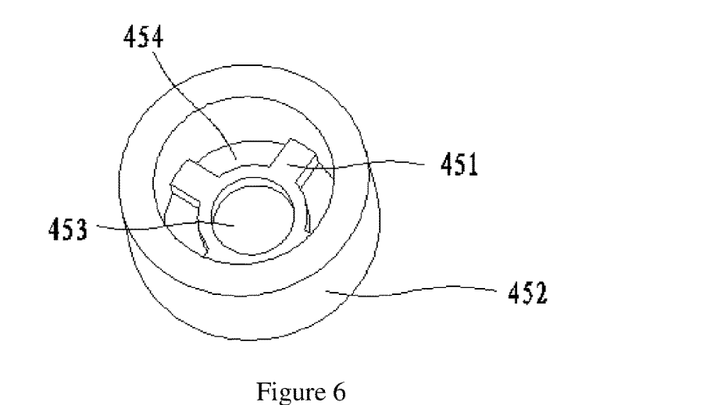
FIG. 6 is a schematic structural view of a clamping ring of the atomizing component shown in FIG. 5.

The clamping member 45 is fixed inside an end of the second connecting tube 44 opposite to the suction nozzle 1, combined with FIG. 6, the clamping member 45 mainly comprises a main body 451 and a connecting ring 452, one end of the connecting ring 452 is fixed to the main body 451 while the other end of the connecting ring 452 extends toward a side close to the suction nozzle 1, an outer side wall of the connecting ring 452 is abutted against an inner side wall of the second connecting tube 44 and makes the clamping member 45 to be interference fitted with the second connecting tube 44.

Specifically, the main body 451 is generally a disc-like structure, the clamping member 45 is provided with a perforation 453 for the ventilation tube 22 to pass through and a plurality of e-liquid inlet holes 454 for adding the e-liquid, the plurality of the e-liquid inlet holes 454 are distributed around the perforation 453. Since the connecting mechanism 4 is fixed to the e-liquid filling hole of the e-liquid storage sleeve 21 in the present embodiment, the e-liquid inlet holes 454 on the main body 451 can facilitate the user to add the e-liquid.

Figure 8:
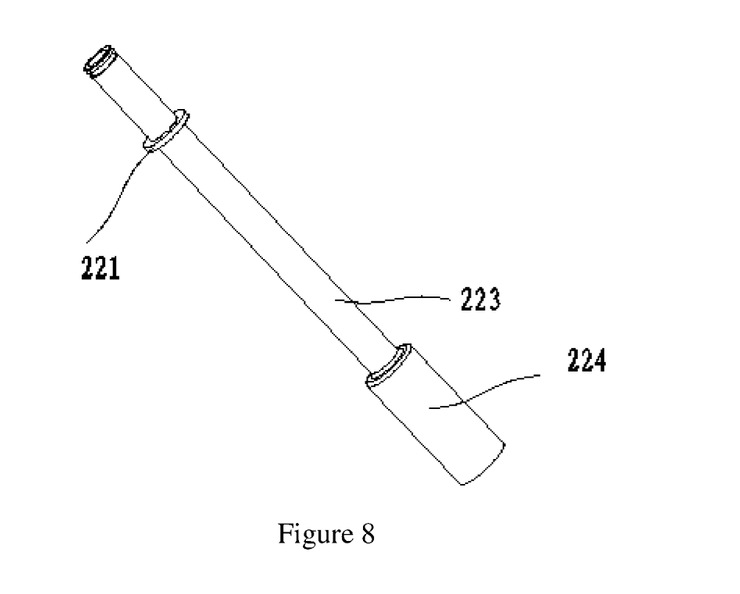
FIG. 8 is a schematic structural view of the ventilation tube of the atomizing component shown in FIG. 5.

Preferably, referring to FIGS. 5 and 8, a limit projection 221 is convexly defined on an outer side wall of the ventilation tube 22, the limit projection 221 is abutted against a side edge of an end of the perforation 453, the end of the perforation 453 is opposite to the suction nozzle 1. The limit projection 221 is configured for limiting the ventilation tube 22 to moving toward a side close to the suction nozzle 1, for instance, when the atomizing core 3 is replaced, the ventilation tube 22 is forced to move toward the side close to the suction nozzle 1, and the limit projection 221 can prevent the ventilation tube 22 from moving toward the side close to the suction nozzle 1, thereby ensuring the stability of the connection between the ventilation tube 22 and the atomizing core 3.

Figure 7:
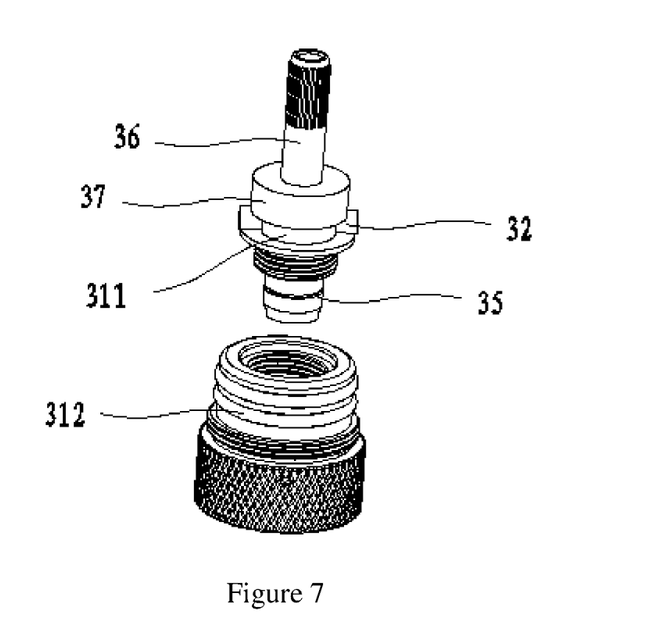
FIG. 7 is a schematic structural view of the atomizing core of the atomizing component shown in FIG. 5.
Figure 9:
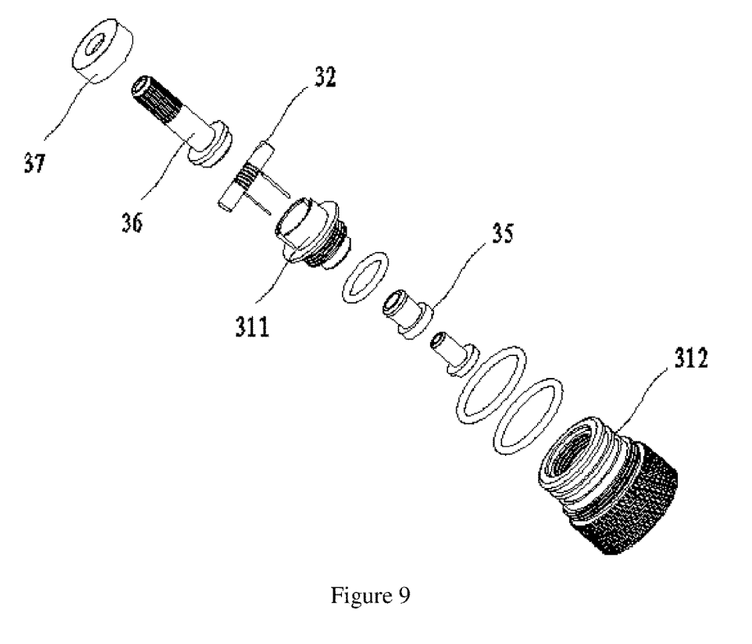
FIG. 9 is an exploded view of the atomizing core of the atomizing component shown in FIG. 5.

As shown in FIGS. 7 and 9, the atomizing core 3 comprises an atomizing sleeve 31, a heating wire assembly 32, an atomizing chamber 34 (as shown in FIG. 5), an atomizing electrode assembly 35, a pressing member 36, and a sealing ring 37.

The atomizing sleeve 31 comprises a first case 311 and a second case 312 which are detachably connected to each other, the first case 311 is defined within the e-liquid storage sleeve 21, the heating wire assembly 32 is mounted in mounting grooves 314 of the first case 311. One end of the second case 312 is located inside the e-liquid storage sleeve 21 and is detachably connected to the first case 311 while the other end of the second case 312 extending outside the e-liquid storage sleeve 21 is detachably connected to the battery assembly; the end of the second case 312 extending outside the e-liquid storage sleeve 21 is provided with an air inlet hole 313.

In the present embodiment, the atomizing sleeve 31 is an external electrode electrically connected to the battery assembly, and the atomizing electrode assembly 35 comprises an insulating member and an inner electrode (both are not labeled in figures) which are successively embedded in the atomizing sleeve 31 from outside to inside, the inner electrode is electrically connected to the battery assembly.

It is to be understood that, in other embodiments, the atomizing electrode assembly 35 may also be made of other conductive structures, such as the atomizing sleeve 31, which is a non-conductive material, and the atomizing electrode assembly 35 comprises an outer electrode which is electrically connected to the battery assembly, an insulating member, and an internal electrode which is electrically connected to the battery assembly, the outer electrode, the insulating member and the internal electrode are embedded in the atomizing sleeve 31 from outside to inside.

The pressing member 36 is generally a hollow structure and is sleeved on an end of the first case 311 close to the suction nozzle 1, one end of the pressing member 36 is abutted against the heating wire assembly 32 to fix the heating wire assembly 32, the other end of the pressing member 36 is abutted against the ventilation tube 22 to prevent the ventilation tube 22 from moving toward a side opposite to the suction nozzle 1.

Specifically, as shown in FIG. 8, in the present embodiment, the ventilation tube 22 comprises a first tube 223 and a second tube 224 connected to each other, and the diameter of the first tube 223 is smaller than the diameter of the second tube 224. The first tube 223 is formed at one end of the suction nozzle 22 near the suction nozzle 1, and the first tube 223 passes through the perforation 453 of the clamp member 45; the second tube body 224 is an end of the ventilation tube 22 opposite to the suction nozzle 1, the second tube 224 is defined outside the pressing member 36 so that the pressing member 36 is abutted against a connection of the first body 223 and the second body 224 to prevent the ventilation tube 22 from moving to the side opposite to the suction nozzle 1.

The sealing ring 37 is roughly a ring structure which is sleeved on a connection between the pressing member 36 and the first case 311 to prevent the e-liquid from leaking from the connection between the pressing member 36 and the first case 311, the second tube 224 of the ventilation tube 22 is sleeved from an end of the pressing member 36 and then abutted against the sealing ring 37, so as to prevent the sealing ring 37 moving.

In view of the above, the embodiment of the atomizing component and the electronic cigarette of the present invention has the following advantageous effects:

(1) One end of the ventilation tube near the suction nozzle extends outside the e-liquid filling hole, namely, the smoke emitting outlet of the ventilation tube and the e-liquid filling hole of the e-liquid storage sleeve are positioned on planes with different heights, so that the smoke emitting outlet of the ventilation tube is higher than the e-liquid filling hole, when the atomizing component is placed vertically to add smoke from the e-liquid filling hole. An outer side wall of the ventilation tube blocks the e-liquid so that the e-liquid can be prevented from splashing into the ventilation tube even if the e-liquid splash occurs accidentally during the addition of the e-liquid; and one end of the e-liquid storage sleeve is detachable connected to the atomizing core so that it can be easily replaced when the atomizing core is damaged, and it also avoids problems, such as, a battery damage, a short circuit and other issues, which are caused by that the e-liquid easily leaks from the atomizing core into the battery assembly due to frequent removals of the atomizing core, when the e-liquid filling hole is provided at an insertion opening of the e-liquid storage sleeve at the atomizing core. Meanwhile, the means of adding e-liquid at the suction nozzle allows the atomizing assembly to be placed directly on a support subject to add the e-liquid when the e-liquid is added, thereby facilitating the use and more in accordance with a user's habit.

(2) Since the height difference between the smoke emitting outlet of the ventilation tube and the e-liquid filling hole of the e-liquid storage sleeve is 1.5 mm, the smoke emitting outlet of the ventilation tube is physically separated from the e-liquid filling hole of the e-liquid storage sleeve and has a distinct position, it can be convenient for the user to add e-liquid.

(3) The e-liquid storage sleeve is provided with a fastening element at a position insertedly connected to the atomizing core, the fastening element is arranged outside the e-liquid storage sleeve, and the fastening element can not only prevent an expansion of the e-liquid storage sleeve, but also can enhance connection strength between the e-liquid storage sleeve and the atomizing core, so as to prevent the atomizing core from dropping from the e-liquid storage sleeve.

While the present invention has been described with reference to preferred embodiments, however, the present invention is not limited to above-mentioned embodiments, and to a person skilled in the art, the invention can have various changes and variations. Those modifications, improvements and equivalent substitutions, which do not depart from the scope of the spirit and the principle of the present invention, should be comprised within the scope of the present invention.

The invention claimed is:

1. An atomizing component configured to form an electronic cigarette with a battery assembly, comprising a light-permeable e-liquid storage sleeve (21), wherein an atomizing core (3) is detachably connected to an end of the e-liquid storage sleeve (21), a fastening element (5) configured for restricting radial expansion of the e-liquid storage sleeve (21) is sleeved at a position of the e-liquid storage sleeve (21), the position of the e-liquid storage sleeve (21) is configured to be insertedly connected to the atomizing core (3);

wherein an e-liquid filling hole is defined on one end surface of the other end of the e-liquid storage sleeve (21), a connecting mechanism (4) is defined at the e-liquid filling hole, one end of the connecting mechanism (4) is connected to the e-liquid storage sleeve (21), the other end of the connecting mechanism (4) is detachably connected to a suction nozzle (1); a ventilation tube (22) is sleeved in the e-liquid storage sleeve (21), two ends of the ventilation tube (22) are elastically and hermetically connected to the atomizing core (3) and the connecting mechanism (4), respectively, an e-liquid storage chamber (23) for storing e-liquid is formed between the ventilation tube (22) and the e-liquid storage sleeve (21);

wherein an end of the ventilation tube (22) opposite to the atomizing core (3) is provided with a smoke emitting outlet in communication with the suction nozzle (1), the end of the ventilation tube (22) provided with the smoke emitting outlet extends from the e-liquid filling hole so that the smoke emitting outlet of the ventilation tube (22) is higher than the e-liquid filling hole when the atomizing component is placed vertically to add e-liquid; and wherein the atomizing core (3) comprises an atomizing sleeve (31), an end of the atomizing sleeve (31) extends outside the e-liquid storage sleeve (21) to detachably connect to the battery assembly, the end of the atomizing sleeve (31) is provided with an atomizing electrode assembly (35) electrically connected to the battery assembly, an atomizing chamber (34) is formed in the atomizing sleeve (31), and a heating wire assembly (32) electrically connected to the atomizing electrode assembly (35) is received in the atomizing chamber (34).

2. The atomizing component according to claim 1, wherein the smoke emitting outlet of the ventilation tube (22) is at least 1.5 mm higher than the e-liquid filling hole when the atomizing component is placed vertically to add the e-liquid.

3. The atomizing component according to claim 1, wherein the suction nozzle (1) is provided with a condensation chamber (12) communicating with the ventilation tube (22), a chamber wall of the condensation chamber (12) is provided with an air outlet (11) for discharging smoke, so that condensed e-liquid can be stored in the condensation chamber (12) when the smoke atomized by the heating wire assembly (32) flows to the air outlet (11) through the ventilation tube (22).

4. The atomizing component according to claim 1, wherein the connecting mechanism (4) comprises a first connecting tube (41), the ventilation tube (22) extends into the first connecting tube (41) and is detachably connected to an inner side wall of the first connecting tube (41), and an outer side wall of an end of the first connecting tube (41) is detachably connected to the suction nozzle (1), the end of the first connecting tube (41) is close to the suction nozzle (1).

5. The atomizing component according to claim 4, wherein the connecting mechanism (4) further comprises a sealing circle piece (42) and a pressing piece (43) which are respectively fixed to an inner side wall of the first connecting tube (41), the sealing circle piece (42) is elastically abutted against at an end of the ventilation tube (22), the pressing piece (43) is defined at a side of the sealing circle piece (42) facing toward the suction nozzle (1) and is abutted against the sealing circle piece (42).

6. The atomizing component according to claim 1, wherein the connecting mechanism (4) comprises a second connecting tube (44) arranged outside the e-liquid storage sleeve (21), an end of the second connecting tube (44) extending outside the e-liquid storage sleeve (21) is detachably connected to the suction nozzle (1), the second connecting tube (44) is provided with a clamping member (45) for fixing the ventilation tube (22); the clamping member (45) is provided with a perforation (453) for the ventilation tube (22) to pass through, and a plurality of e-liquid inlet holes (454) for adding the e-liquid, the plurality of the e-liquid inlet holes (454) are distributed around the perforation (453).

7. The atomizing component according to claim 6, wherein the clamping member (45) comprises a main body (451) and a connecting ring (452), an end of the connecting ring (452) is fixed on a periphery of the main body (451), an outer side wall of the connecting ring (452) is abutted against an inner side wall of the second connecting tube (44), the perforation (453) and the e-liquid inlet holes (454) are both defined on the main body (451), a limit projection (221) is convexly defined on an outer side wall of the ventilation tube (22), the limit projection (221) is configured for limiting the ventilation tube (22) to moving toward a side close to the suction nozzle (1), the limit projection (221) is abutted against a side edge of an end of the perforation (453), the end of the perforation (453) is opposite to the suction nozzle (1).

8. The atomizing component according to claim 1, wherein the atomizing core (3) further comprises an atomizing cover (33) arranged on the atomizing sleeve (31) and the ventilation tube (22) and abutted against the heating wire assembly (32), one end of the ventilation tube (22) passes through the atomizing cover (33) and extends into the atomizing chamber (34).

9. The atomizing component according to claim 8, wherein one end of the ventilation tube (22) is detachably connected to the atomizing cover (33), the end of the ventilation tube (22) is opposite to the suction nozzle (1), a stopper flange (222) is convexly defined on an outer side wall of the ventilation tube (22), the stopper flange (222) is configured for limiting the ventilation tube (22) to moving toward a side opposite to the suction nozzle (1), the stopper flange (222) is abutted against an end of the atomizing cover (33).

10. The atomizing component according to claim 1, wherein the atomizing sleeve (31) comprises a first case (311) and a second case (312) which are detachably connected to each other, the first case (311) is defined within the e-liquid storage sleeve (21), the heating wire assembly (32) is mounted on the first case (311), one end of the second case (312) extending outside the e-liquid storage sleeve (21) is detachably connected to the battery assembly; and wherein the atomizing core (3) further comprises a pressing member (36) abutted against the heating wire assembly (32), and a sealing ring (37) sleeved on a joint between the pressing member (36) and the first case (311), the ventilation tube (22) is sleeved outside the pressing piece (43) and elastically abutted against the sealing ring (37), the pressing member (36) is a hollow structure and is communicated with the ventilation tube (22).

11. The atomizing component according to claim 1, wherein an air inlet hole (313) is defined on a peripheral wall of an end of the atomizing sleeve (31) extending outside the e-liquid storage sleeve (21), the air inlet hole (313) communicated with the atomizing chamber (34) is configured for inletting air and discharging e-liquid in the atomizing chamber.

12. The atomizing component according to claim 1, wherein an end of a side wall of the atomizing sleeve (31) close to the suction nozzle (1) is axially provided with two mounting grooves (314), the two mounting grooves (314) are spaced from each other, arranged opposite to each other and communicated with the e-liquid storage chamber (23), the heating wire assembly (32) is arranged in the two mounting grooves (314).

13. An electronic cigarette comprising a battery assembly and an atomizing component which are connected to each other, wherein the atomizing component comprises a light-permeable e-liquid storage sleeve (21), an atomizing core (3) is detachably connected to an end of the e-liquid storage sleeve (21), a fastening element (5) configured for restricting radial expansion of the e-liquid storage sleeve (21) is sleeved at where the e-liquid storage sleeve (21) is insertedly connected to the atomizing core (3);

wherein an e-liquid filling hole is defined on one end surface of the other end of the e-liquid storage sleeve (21), a connecting mechanism (4) is defined at e-liquid filling hole, one end of the connecting mechanism (4) is connected to the e-liquid storage sleeve (21), the other end of the connecting mechanism (4) is detachably connected to a suction nozzle (1); a ventilation tube (22) is sleeved in the e-liquid storage sleeve (21), two ends of the ventilation tube (22) are elastically and hermetically connected to the atomizing core (3) and the connecting mechanism (4), respectively, an e-liquid storage chamber (23) for storing the e-liquid is formed between the ventilation tube (22) and the e-liquid storage sleeve (21);

wherein an end of the ventilation tube (22) opposite to the atomizing core (3) is a smoke emitting outlet in communication with the suction nozzle (1), the end of the ventilation tube (22) which is provided with the smoke emitting outlet extends from the e-liquid filling hole so that the smoke emitting outlet of the ventilation tube (22) is higher than the e-liquid filling hole when the atomizing component is placed vertically to add e-liquid; and wherein the atomizing core (3) comprises an atomizing sleeve (31), an end of atomizing sleeve (31) extends outside the e-liquid storage sleeve (21) to detachably connected to the battery assembly, the end of the atomizing sleeve (31) is provided with an atomizing electrode assembly (35) electrically connected to the battery assembly, an atomizing chamber (34) is formed in the atomizing sleeve (31), and a heating wire assembly (32) electrically connected to the atomizing electrode assembly (35) is received in the atomizing chamber (34).

\* \* \* \* \*